United States Patent
Park et al.

(10) Patent No.: US 8,535,918 B2
(45) Date of Patent: Sep. 17, 2013

(54) PREPARING METHOD FOR (S)-3HYDROXYBUTYRIC ACID AND (S)-3 HYDROXYBUTYRATE ESTER USING RECOMBINANT MICROORGANISM

(75) Inventors: Si Jae Park, Daejeon (KR); Sang Hyun Lee, Daejeon (KR)

(73) Assignee: LG Chem, Ltd., Soeul (KR)

( * ) Notice: Subject to any disclaimer, the term of this patent is extended or adjusted under 35 U.S.C. 154(b) by 348 days.

(21) Appl. No.: 12/733,026

(22) PCT Filed: Jun. 10, 2008

(86) PCT No.: PCT/KR2008/003217
§ 371 (c)(1),
(2), (4) Date: Apr. 22, 2010

(87) PCT Pub. No.: WO2009/020279
PCT Pub. Date: Feb. 12, 2009

(65) Prior Publication Data
US 2010/0209983 A1 Aug. 19, 2010

(30) Foreign Application Priority Data
Sep. 8, 2007 (KR) ........................ 10-2007-0080109

(51) Int. Cl.
C12P 7/62 (2006.01)
(52) U.S. Cl.
USPC ....... 435/135; 435/69.1; 435/242; 435/320.1; 435/141
(58) Field of Classification Search
None
See application file for complete search history.

(56) References Cited

U.S. PATENT DOCUMENTS

| | | | | |
|---|---|---|---|---|
| 7,541,173 B2 * | 6/2009 | Bramucci et al. | .......... | 435/252.3 |
| 7,659,104 B2 * | 2/2010 | Bramucci et al. | .......... | 435/252.1 |
| 8,017,364 B2 * | 9/2011 | Bramucci et al. | ............. | 435/160 |
| 8,048,666 B1 * | 11/2011 | Green et al. | ................ | 435/252.3 |
| 8,067,667 B2 * | 11/2011 | Cigan et al. | .................... | 800/274 |

FOREIGN PATENT DOCUMENTS

WO WO 2007/041269 4/2007

OTHER PUBLICATIONS

Manchak et al. (Microbiol., 1994, vol. 140, pp. 953-963).*

Lee et al., "Biosynthesis of enantiopure (S)-3-hydroxybutyric acid in metabolically engineered *Escherichia coli*", Appl. Microbiol. Biotechnol., vol. 79, pp. 633-641, 2008.
Liu et al., "Microbial production of *R*-3-hydroxybutyric acid by recombinant *E. coli* harboring genes of *phbA*, *phbB*, and *tesB*", Appl. Microbiol. Biotechnol., vol. 76, pp. 811-818, 2007.
Lee et al., "Metabolic engineering of *Escherichia coli* for production of enantiomerically pure (R)-(−)-hydroxycarboxylic acids", Applied and Environmental Microbiology, vol. 69, No. 6, pp. 3421-3426, 2003.
Gao et al., "Enhanced production of D-(−)-3-hydroxybutyric acid by recombinant *Escherichia coli*", FEMS Microbiology Letter, vol. 213(1), pp. 59-65, 2002.
Colby et al., "Purification and properties of 3-hydroxybutyryl-coenzyme A dehydrogenase from *Clostridium beijerinckii* (*Clostridium butylieum*) NRRL B593", Applied and Environemental Microbiology, vol. 58, No. 10, pp. 3297-3302, 1992.
Boynton et al. "Cloning, sequencing, and expression of clustered genes encoding β- Hydroxybutyryl-Coenzyme A (CoA) dehudrogenase, Crotonase, and Butryl-CoA Dehydrogenase from *Clostridium Acetobutlicum* ATCC 824", Journal of Bacteriology, vol. 178, No. 11, Jun. 1996, p. 3015-3024.
Liu et al. "Microbial producto of R-3-hydroxybutyric acid by recombinant *E. coli* harboring genes of phbA, phbB, and tesB", Appl. Microbiol Bicotechnol, 2007, vol. 76, pp. 811-818.

* cited by examiner

*Primary Examiner* — Hope Robinson
(74) *Attorney, Agent, or Firm* — McKenna Long & Aldridge, LLP

(57) ABSTRACT

A method of synthesizing optically-active (S)-3-hydroxybutyric acid and (S)-3-hydroxybutyrate ester using a mutated microorganism is provided. More particularly, a mutated microorganism for preparing (S)-3-hydroxybutyric acid transformed with a gene encoding β-ketothiolase, a gene encoding (S)-3-hydroxybutyryl CoA dehydrogenase and a gene encoding acyl CoA hydrolase; a method of preparing (S)-3-hydroxybutyric acid using the mutated microorganism; a mutated microorganism for preparing (S)-3-hydroxybutyrate ester transformed with a gene encoding β-ketothiolase, a gene encoding (S)-3-hydroxybutyryl CoA dehydrogenase, a gene encoding acyl CoA hydrolase and a gene encoding lipase; and a method of preparing (S)-3-hydroxybutyrate ester using the mutated microorganism are provided.
Accordingly, (S)-3-hydroxybutyric acid with high optical purity may be produced from acetyl CoA produced in glycolysis of a microorganism by a simple process involving the manipulation of a metabolic pathway by a recombinant gene introduced into the microorganism without using a high-cost metal catalyst or a substrate. Further, (S)-3-hydroxybutyrate ester and lactone of (S)-3-hydroxybutyrate ester may be simply produced from (S)-3-hydroxybutyric acid produced by the above method using lipase.

8 Claims, 10 Drawing Sheets

SEQUENCE LISTING

```
<160> NUMBER OF SEQ ID NOS: 18

<210> SEQ ID NO 1
<211> LENGTH: 1182
<212> TYPE: DNA
<213> ORGANISM: Ralstonia eutropha

<400> SEQUENCE: 1
atgactgacg ttgtcatcgt atccgccgcc cgcaccgcgg tcggcaagtt tggcggctcg      60
ctggccaaga tcccggcacc ggaactgggt gccgtggtca tcaaggccgc gctggagcgc     120
gccggcgtca agcggagca ggtgagcgaa gtcatcatgg ccaggtgct gaccgccggt      180 tcgggccaga accccgcacg ccaggccgcg atcaaggccg gcctgccggc gatggtgccg     240
gccatgacca tcaacaaggt gtgcggctcg ggcctgaagg ccgtgatgct ggccgccaac     300
gcgatcatgg cgggcgacgc cgagatcgtg gtggccggcg gccaggaaaa catgagcgcc     360
gccccgcacg tgctgccggg ctcgcgcgat ggtttccgca tgggcgatgc caagctggtc     420
gacaccatga tcgtcgacgg cctgtgggac gtgtacaacc agtaccacat gggcatcacc     480
gccgagaacg tggccaagga atacggcatc acacgcgagg cgcaggatga gttcgccgtc     540
ggctcgcaga acaaggccga agccgcgcag aaggccggca gtttgacga agagatcgtc     600 ccggtgctga tcccgcagcg caagggcgac ccggtggcct tcaagaccga cgagttcgtg     660
cgccagggcg ccacgctgga cagcatgtcc ggcctcaagc ccgccttcga caaggccggc     720
acggtgaccg cggccaacgc ctcgggcctg aacgacggcg ccgccgcggt ggtggtgatg     780
tcggcggcca aggccaagga actgggcctg accccgctgg ccacgatcaa gagctatgcc     840
aacgccggtg tcgatcccaa ggtgatgggc atgggcccgg tgccggcctc caagcgcgcc     900
ctgtcgcgcg ccgagtggac cccgcaagac ctggacctga tggagatcaa cgaggccttt     960
gccgcgcagg cgctggcggt gcaccagcag atgggctggg acacctccaa ggtcaatgtg    1020
```

```
aacggcggcg ccatcgccat cggccacccg atcggcgcgt cgggctgccg tatcctggtg      1080
acgctgctgc acgagatgaa cgccgtgac gcgaagaagg gcctggcctc gctgtgcatc       1140
ggcggcggca tgggcgtggc gctggcagtc gagcgcaaat aa                          1182

<210> SEQ ID NO 2
<211> LENGTH: 849
<212> TYPE: DNA
<213> ORGANISM: Clostridium acetobutylicum

<400> SEQUENCE: 2
atgaaaaagg tatgtgttat aggtgcaggt actatgggtt caggaattgc tcaggcattt       60
gcagctaaag gatttgaagt agtattaaga gatattaaag atgaatttgt tgatagagga      120
ttagatttta tcaataaaaa tctttctaaa ttagttaaaa aggaaagat agaagaagct       180 actaaagttg aaatcttaac tagaattttcc ggaacagttg accttaatat ggcagctgat     240
tgcgatttag ttatagaagc agctgttgaa agaatggata ttaaaaagca gattttttgct    300 gacttagaca atatatgcaa gccagaaaca attcttgcat caaatacatc atcactttca     360
ataacagaag tggcatcagc aactaaaact aatgataagg ttataggtat gcatttcttt     420
aatccagctc ctgttatgaa gcttgtagag gtaataagag gaatagctac atcacaagaa     480
acttttgatg cagttaaaga gacatctata gcaataggaa aagatcctgt agaagtagca     540
gaagcaccag gatttgttgt aaatagaata ttaataccaa tgattaatga gcagttggt      600 atattagcag aaggaatagc ttcagtagaa gacatagata aagctatgaa acttggagct     660
aatcacccaa tgggaccatt agaattaggt gattttatag gtcttgatat atgtcttgct     720
ataatggatg ttttatactc agaaactgga gattctaagt atagaccaca tacattactt     780
aagaagtatg taagagcagg atggcttgga agaaaatcag gaaaaggttt ctacgattat     840
tcaaaataa                                                             849

<210> SEQ ID NO 3
<211> LENGTH: 1095
<212> TYPE: DNA
<213> ORGANISM: Ralstonia eutropha

<400> SEQUENCE: 3
atgagcatca ggacagtggg catcgtcggt gccggcacca tgggcaatgg catcgcccag      60
gcctgcgcag tggtaggtct caacgtggtg atggtcgaca tcagcgatgc cgccgtgcag     120
aagggtgtcg ccaccgtggc aagcagcctg gaccgtctga tcaagaagga aaagctgacc     180
gaggccgaca aggccagcgc gctggcgcgc atcaagggca gcacctcgta tgacgatctc     240
aaggccaccg atatcgtgat cgaggccgcc accgagaact acgacctgaa ggtcaagatc     300
ctcaagcaga tcgacggcat cgtcggcgag aacgtgatca tcgcgtccaa cacctcgtcg     360
atctcgatca ccaagctggc tgccgtgacc tcgcgcgccg cagccgctc ttgcactagt     420 agcgcaggtt gtggagcagc tagagctagt ggttcgaccg acggcactgg agcgcgcggc    480
accgctttat cggcatgcac ttcttcaacc cggtgccggt gatggcgctg gtggaactga     540
tccgcggcct gcagaccagc gacaccaccc acgccgccgt cgaggccctg tcgaagcagc     600
tcggcaaata cccgatcacg gtcaagaaca gcccgggctt ctgtggtggg tgcggcggca      660
gctccgggac agcttcgtcg agccgtttat gggctagtgc cagttcttgt cgggcccgaa     720
cgtcgtcaac cgcatcctgt gcccgatgat caacgaggcc ttctgcgtgc tgggcgaagg     780
cctggcctcg ccggaagaga gcagcagttg gcgtaggaca cgggctacta gttgctccgg     840
```

-continued

```
aagacgcacg acccgcttcc ggaccggagc ggccttctct tcgacgaagg catgaagctg    900
ggctgcaacc acccgatcgg gccgctggcg ctggctgaca tgatcggcct ggacaccatg    960
ctggccgtga tggaagtgct gtacacggag tttgccgatc cgaagtaccg cccggcgatg   1020
ctgatgcgcg agatggtcgc tgccggctac ctgggccgca agactggccg cggcgtgtac   1080
gtctatagca agtaa                                                    1095
```

<210> SEQ ID NO 4
<211> LENGTH: 1056
<212> TYPE: DNA
<213> ORGANISM: Bacillus cereus

<400> SEQUENCE: 4

```
atgactgaac aagttttatt ttctgttagt gaaaatggcg ttgcgacaat tactttaaac     60
cgtccaaaag cacttaattc tttatcttat gacatgttac aacctatcgg acaaaaactt    120
aaagagtggg aacacgatga gcgtattgca cttatcgtgt taaaaggagc tggcacaaaa    180
ggtttttgtg caggtggcga cattaaaact ctttatgaag cgcgttccaa tgaagtggca    240
ttgcaacatg cagaacgttt ttttgaagaa gagtatgaaa ttgatacata tatttatcaa    300
tatacaaaac cgattattgc ttgtttagat ggaattgtaa tgggcggtgg tgtcggtctt    360
acaaatggtg cgaagtatcg cattgtaact gagcgtacga aatgggcaat gccagagatg    420
aatatcggct tcttcccaga cgtcggagct gcatatttct taaataaagc gcctggatat    480
acaggacgat tcgttgcttt aacagcatct attttaaaag cttctgacgt attatttatt    540
aatgctgcag attactttat gacatctgat tcattaccag agtttcttac tgaacttgaa    600
agtgtaaatt ggcataaaga agatgatgta catactaatt taaaagaagt tattcgtaca    660
tttgcaactg ctccaaactt agaaagcgag ctcgctcctt cattagaagt aatcaattca    720
cattttgctt tcgatacaat tgaagaaatc atccattcat tggagaaaga tgaaagttcc    780
tttgctctaa aaacgaaaga aatactgtta tcaaaatccc ctatttcact aaaagtaaca    840
ttaaaacagt ttattgatgg acaagataaa tccgttgaag aatgtttcgc tacggacctt    900
atacttgcta aaaacttcat gagacatgaa gatttcttcg aaggagtacg ctccgttgtc    960
gttgataaag atcaaaatcc gaattataaa tataaacagt taagtgacgt ttcagaagaa   1020
gatgtgaatc gtttctttaa cttacttaat gcataa                             1056
```

<210> SEQ ID NO 5
<211> LENGTH: 31
<212> TYPE: DNA
<213> ORGANISM: Artificial Sequence
<220> FEATURE:
<223> OTHER INFORMATION: primer

<400> SEQUENCE: 5

```
ggaattcatg actgacgttg tcatcgtatc c                                    31
```

<210> SEQ ID NO 6
<211> LENGTH: 22
<212> TYPE: DNA
<213> ORGANISM: Artificial Sequence
<220> FEATURE:
<223> OTHER INFORMATION: primer

<400> SEQUENCE: 6

```
gtccactcct tgattggctt cg                                              22
```

<210> SEQ ID NO 7
<211> LENGTH: 44
<212> TYPE: DNA
<213> ORGANISM: Artificial Sequence
<220> FEATURE:
<223> OTHER INFORMATION: primer

<400> SEQUENCE: 7
gaagccaatc aaggagtgga catgaaaaag gtatgtgtta tagg     44

<210> SEQ ID NO 8
<211> LENGTH: 32
<212> TYPE: DNA
<213> ORGANISM: Artificial Sequence
<220> FEATURE:
<223> OTHER INFORMATION: primer

<400> SEQUENCE: 8
gctctagatt attttgaata atcgtagaaa cc     32

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9
cgccatatga ctgaacaagt tttattt     27

<210> SEQ ID NO 10
<211> LENGTH: 31
<212> TYPE: DNA
<213> ORGANISM: Artificial Sequence
<220> FEATURE:
<223> OTHER INFORMATION: primer

<400> SEQUENCE: 10
ataggatcct tatgcattaa gtaagttaaa g     31

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
tataagatct caaccatcat cgatgaattg t     31

<210> SEQ ID NO 12
<211> LENGTH: 30
<212> TYPE: DNA
<213> ORGANISM: Artificial Sequence
<220> FEATURE:
<223> OTHER INFORMATION: primer

<400> SEQUENCE: 12
tattctagaa acaccccttg tattactgtt     30

<210> SEQ ID NO 13
<211> LENGTH: 127
<212> TYPE: DNA
<213> ORGANISM: Artificial Sequence
<220> FEATURE:
<223> OTHER INFORMATION: EZ::TN<KAN2>

<400> SEQUENCE: 13

```
tacacatctc aaccatcatc gatgaattgt gtctcaaaat ctctgatgtt acattgcaca    60
agataaaaat atatcatcat gaacaataaa actgtctgct tacataaaca gtaatacaag   120
gggtgtt                                                             127
```

<210> SEQ ID NO 14
<211> LENGTH: 36
<212> TYPE: DNA
<213> ORGANISM: Artificial Sequence
<220> FEATURE:
<223> OTHER INFORMATION: primer

<400> SEQUENCE: 14

```
atacatatga aaaggtatg tgttataggt gcaggt                               36
```

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15

```
ataggattct tattttgaat aatcgtagaa acsttt                              36
```

<210> SEQ ID NO 16
<211> LENGTH: 41
<212> TYPE: DNA
<213> ORGANISM: Artificial Sequence
<220> FEATURE:
<223> OTHER INFORMATION: primer

<400> SEQUENCE: 16

```
gaagccaatc aaggagtgga catgagcatc aggacagtgg g                        41
```

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17

```
atactcgagt tacttgctat agacgtacac gccgcggcc                           39
```

<210> SEQ ID NO 18
<211> LENGTH: 41
<212> TYPE: DNA
<213> ORGANISM: Artificial Sequence
<220> FEATURE:
<223> OTHER INFORMATION: primer

<400> SEQUENCE: 18

```
atactcgagt tattttgaat aatcgtagaa accttttcct g                        41
```

PREPARING METHOD FOR (S)-3HYDROXYBUTYRIC ACID AND (S)-3 HYDROXYBUTYRATE ESTER USING RECOMBINANT MICROORGANISM

This application claims the benefit of PCT/KR2008/003217 filed on Jun. 10, 2008 and Korean Patent Application No. 10-2007-0080109 filed on Aug. 9, 2007, all of which are hereby incorporated herein by reference for all purposes in their entirety.

TECHNICAL FIELD

The present invention relates to a method of preparing optically-active (S)-3-hydroxybutyric acid and (S)-3-hydroxybutyrate ester using a recombinant microorganism. More particularly, the present invention relates to a recombinant microorganism for preparing (S)-3-hydroxybutyric acid, which is transformed with a gene encoding β-ketothiolase, a gene encoding (S)-3-hydroxybutyryl CoA dehydrogenase and a gene encoding acyl CoA hydrolase; a method of preparing (S)-3-hydroxybutyric acid using the recombinant microorganism; a recombinant microorganism for preparing (S)-3-hydroxybutyrate ester, which is transformed with a gene encoding β-ketothiolase, a gene encoding (S)-3-hydroxybutyryl CoA dehydrogenase, a gene encoding acyl CoA hydrolase and a gene encoding lipase; and a method of preparing (S)-3-hydroxybutyrate ester using the recombinant microorganism.

BACKGROUND ART (S)-3-hydroxybutyric acid and (S)-3-hydroxylbutyrate ester are very effective chiral intermediates and have a wide range of applications such as in plastic materials, aromatics, medicines and agrichemicals (Speciality Chemicals Magazine, April:39, 2004). For example, they may be used to synthesize (S)-1,3-butanediol, an intermediate for preparing various antibiotics and pheromones by reduction of ethyl-(S)-3-hydroxybutyrate (T. Ferreira et al., Tetrahedron, 46:6311, 1990), and may be used as a precursor of a herbicide, (S)-sulcatol (K. Mori et al., Tetrahedron, 37:1341, 1981), a precursor of a b-lactam antibiotic, Carbapeneme (T. Chiba et al., Chemistry letters, 16:2187, 1987), and a precursor of a vitamin-like nutrient, L-carnitine (B. N. Zhou et al., Journal of American Chemical Society, 105:5925, 1983).

There is a conventional method for preparing ester such as asymmetric reductive hydrogenation of a prochiral precursor, 3-ketoester, with a catalyst, diphosphine-ruthenium (R. Noyori et al., Journal of the American Chemical Society, 109: 5856, 1987), but this method requires a very expensive metal catalyst, a pure substrate and a very high-pressure reactor. Further, production of ethyl (S)-3-hydroxybutyrate with a yield of 58% and an optical purity of 94% ee by biocatalytic reduction of b-ketoester using yeast as a whole-cell catalyst exhibits low optical activity due to various oxidoreductases present in microorganisms (Tetrahedron Letters, 34:3949, 1993).

It has been reported that optically-active (R)-3-hydroxyalkanoate is biosynthesized from glucose by manipulating a metabolic pathway of a microorganism (Lee et al., Biotechnol Bioeng, 65:363, 1999; Lee and Lee., Appl Envron Microbiol, 69:1295, 2003; Gao et al., FEMS Microbiol Lett, 213:59, 2002). There are two routes to produce (R)-3-hydroxyalkanoate: one is autolysis of a biodegradable polymer, polyhydroxyalkanoate (Lee et al., Biotechnol Bioeng, 65:363, 1999; Lee and Lee., Appl Environ Microbial, 69:1295, 2003); and the other is removal of CoA from (R)-3-hydroxylalkanoyl CoA synthesized from glucose, not the autolysis of a biodegradable polymer, to produce (R)-3-hydroxyalkanoate (Gao et al., FEMS Microbiol Lett, 213:59, 2002). In the second route, (R)-3-hydroxybutyryl CoA is produced from glucose using β-ketothiolase (PhaA) and (R)-3-hydroxybutyryl CoA reductase (PhaB), and then CoA is removed from the (R)-3-hydroxybutyryl CoA using phosphotransbutylase (ptb) and butyrate kinase (BuK) (Gao et al., FEMS Microbiol Lett, 213:59, 2002).

While chemical and biocatalytic routes for producing optically-active (S)-3-hydroxybutyrate have been reported, a route for producing optically-active (S)-3-hydroxybutyric acid and (S)-3-hydroxybutyrate ester biosynthesized from glucose by manipulating a metabolic pathway of a microorganism had not yet been reported.

Therefore, the present inventors tried to biosynthesize optically-active (S)-3-hydroxybutyric acid and (S)-3-hydroxybutyrate ester and finally found that they are biosynthesized with high optical purity from acetyl CoA produced in glycolysis of a microorganism by a simple process involving the manipulation of a metabolic pathway by a recombinant gene introduced into the microorganism without using an expensive metal catalyst or a substrate. This discovery led them to the present invention.

DISCLOSURE

Technical Problem

The present invention is directed to providing a recombinant microorganism for preparing (S)-3-hydroxybutyric acid, and a method of preparing (S)-3-hydroxybutyric acid comprising culturing the recombinant microorganism.
The present invention is further directed to proving a recombinant microorganism for preparing (S)-3-hydroxybutyrate ester, and a method of preparing (S)-3-hydroxybutyrate ester comprising culturing the recombinant microorganism.

Technical Solution

In one aspect, the present invention provides a recombinant microorganism for preparing (S)-3-hydroxybutyric acid, which is transformed with a gene encoding β-ketothiolase, a gene encoding (S)-3-hydroxybutyryl CoA dehydrogenase and a gene encoding acyl CoA hydrolase.

In another aspect, the present invention provides a recombinant microorganism for preparing (S)-3-hydroxybutyric acid, which is transformed with a gene encoding β-ketothiolase, a gene encoding (S)-3-hydroxybutyryl CoA dehydrogenase, a gene encoding phosphotransbutylase (ptb) and a gene encoding butyrate kinase (Buk).

In still another aspect, the present invention provides a method of preparing (S)-3-hydroxybutyric acid characterized by culturing the recombinant microorganism. In yet another aspect, the present invention provides a method of preparing (S)-3-hydroxybutyric acid characterized by reacting a culture or cell extract of the recombinant microorganisms with a substrate selected from the group consisting of acetyl CoA, acetoacetyl CoA and (S)-3-hydroxybutyryl CoA.

In yet another aspect, the present invention provides a recombinant microorganism for preparing (S)-3-hydroxybutyrate ester, which is transformed with a gene encoding β-ketothiolase, a gene encoding (S)-3-hydroxybutyryl CoA dehydrogenase, a gene encoding acyl CoA hydrolase and a gene encoding lipase.

In yet another aspect, the present invention provides a method of preparing (S)-3-hydroxybutyrate ester characterized by culturing the recombinant microorganism.

Advantageous Effects

The present invention provides methods of biosynthesizing (S)-3-hydroxybutyric acid and (S)-3-hydroxybutyrate ester with high optical purity from acetyl CoA produced in glycolysis of a microorganism by a simple process involving the manipulation of a metabolic pathway by a recombinant gene introduced into the microorganism without using an expensive metal catalyst or a substrate.

MODE FOR INVENTION (S)-3-hydroxybutyric acid prepared by a method of the present invention is an optically-active compound with different chirality from (R)-3-hydroxybutyric acid, as shown in Formula 1.
[Formula 1]

[Formula 1]

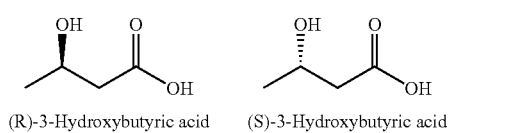

(R)-3-Hydroxybutyric acid    (S)-3-Hydroxybutyric acid

Figure 1:
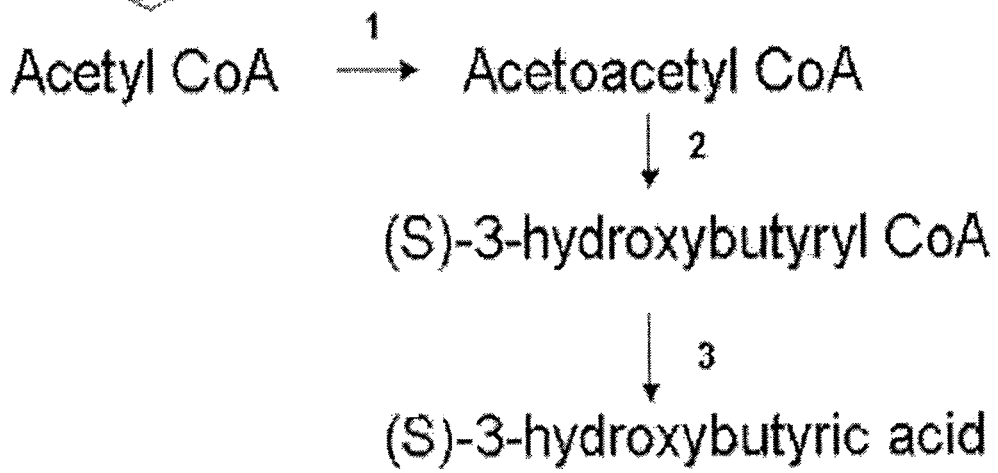
FIG. 1 shows a biosynthetic pathway of (S)-3-HB.

To prepare (S)-3-hydroxybutyric acid, a recombinant microorganism transformed with a gene encoding β-ketothiolase, a gene encoding (S)-3-hydroxybutyryl CoA dehydrogenase, and a gene encoding acyl CoA hydrolase is provided.
According to the present invention, the recombinant microorganism transformed with a gene encoding β-ketothiolase, a gene encoding (S)-3-hydroxybutyryl CoA dehydrogenase and a gene encoding acyl CoA hydrolase produces (S)-3-hydroxybutyric acid through a biosynthetic pathway shown in FIG. 1.
First, acetyl CoA is produced from glucose through glycolysis, and converted into acetoacetyl CoA by β-ketothiolase, the acetocetyl CoA is then converted into (S)-3-hydroxybutyryl CoA by (S)-3-hydroxybutyryl CoA dehydrogenase, and finally the (S)-3-hydroxybutyryl CoA is converted into (S)-3-hydroxybutyric acid by acyl CoA hydrolase.

Figure 2:
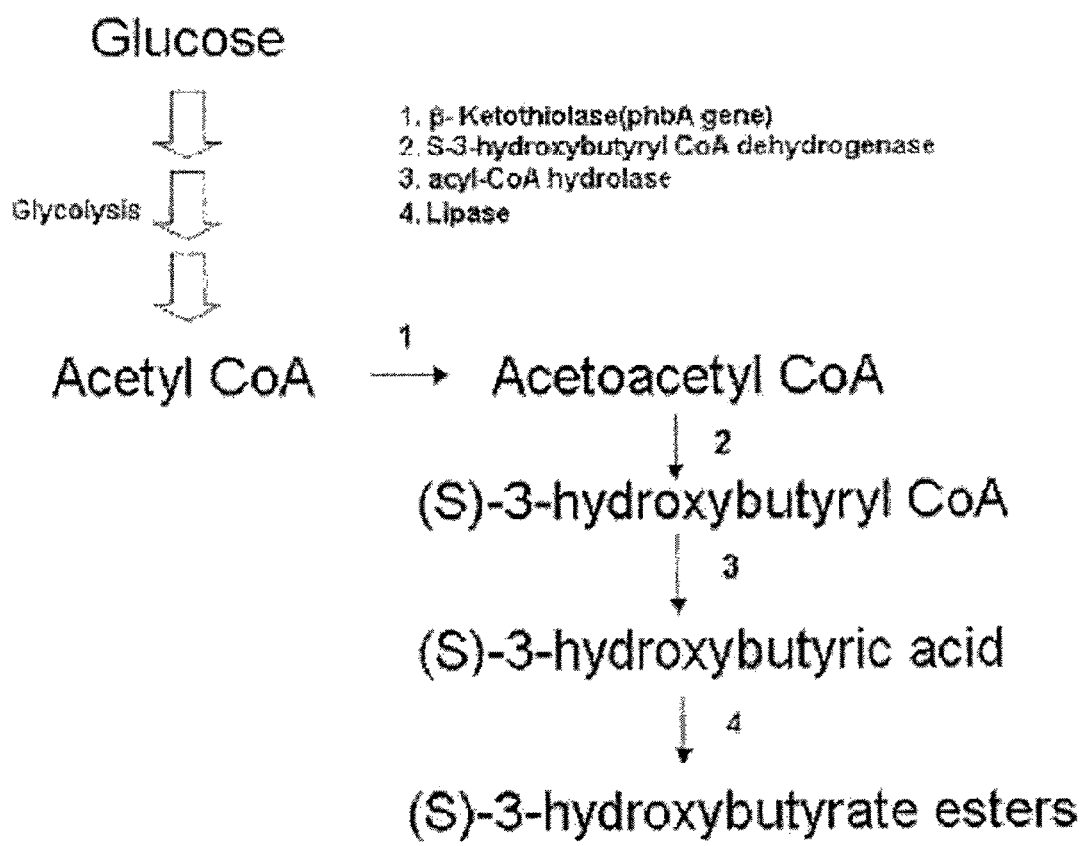
FIG. 2 shows a biosynthetic pathway of (S)-3-HB.

The present invention also provides a recombinant microorganism for preparing (S)-3-hydroxybutyric acid transformed with a gene encoding β-ketothiolase, a gene encoding (S)-3-hydroxybutyryl CoA dehydrogenase, a gene encoding phosphotransbutylase (ptb) and a gene encoding butyrate kinase (Buk).
According to the present invention, the recombinant microorganism for preparing (S)-3-hydroxybutyric acid transformed with a gene encoding β-ketothiolase, a gene encoding (S)-d-hydroxybutyryl CoA dehydrogenase, a gene encoding phosphotrasnsbutylase (ptb) and a gene encoding butyrate kinase (Buk) produces (S)-3-hydroxybutyric acid through a pathway shown in FIG. 2.
When acetyl CoA is produced from glucose through glycolysis, the acetyl CoA is converted into acetoacetyl CoA by β-ketothiolase, the acetoacetyl CoA is then converted into (S)-3-hydroxybutyryl CoA by (S)-3-hydroxybutyryl CoA dehydrogenase, the (S)-3-hydroxybutyryl CoA is converted into (S)-3-hydroxybutyryl phosphate by phosphotransbutylase (Ptb) or phosphotransacetylase (Pta), and finally the (S)-3-hydroxybutyryl phosphate is converted into (S)-3-hydroxybutyric acid by butyrate kinase (Buk) or propionate kinase (Puk) (see FIG. 2).

In one embodiment of the present invention, the recombinant microorganism for preparing (S)-3-hydroxybutyric acid may be transformed with at least one recombinant vector comprising at least one selected from the group consisting of a gene encoding β-ketothiolase, a gene encoding (S)-3-hydroxybutyryl CoA dehydrogenase and a gene encoding acyl CoA hydrolase.

For example, the recombinant microorganism for preparing (S)-3-hydroxybutyric acid may be transformed with a recombinant vector containing a gene encoding β-ketothiolase, a recombinant vector containing a gene encoding (S)-3-hydroxybutyryl CoA dehydrogenase and a recombinant vector containing a gene encoding acyl CoA hydrolase. Alternatively, the recombinant microorganism for preparing (S)-3-hydroxybutyric acid may be transformed with a recombinant vector containing genes encoding β-ketothiolase and (S)-3-hydroxybutyryl CoA dehydrogenase and a recombinant vector containing a gene encoding acyl CoA hydrolase.

In one embodiment of the present invention, the gene encoding β-ketothiolase, the gene encoding (S)-3-hydroxybutyryl CoA dehydrogenase and the gene encoding acyl CoA hydrolase may be inserted into a chromosome of the recombinant microorganism for preparing (S)-3-hydroxybutyric acid.

Figure 3:
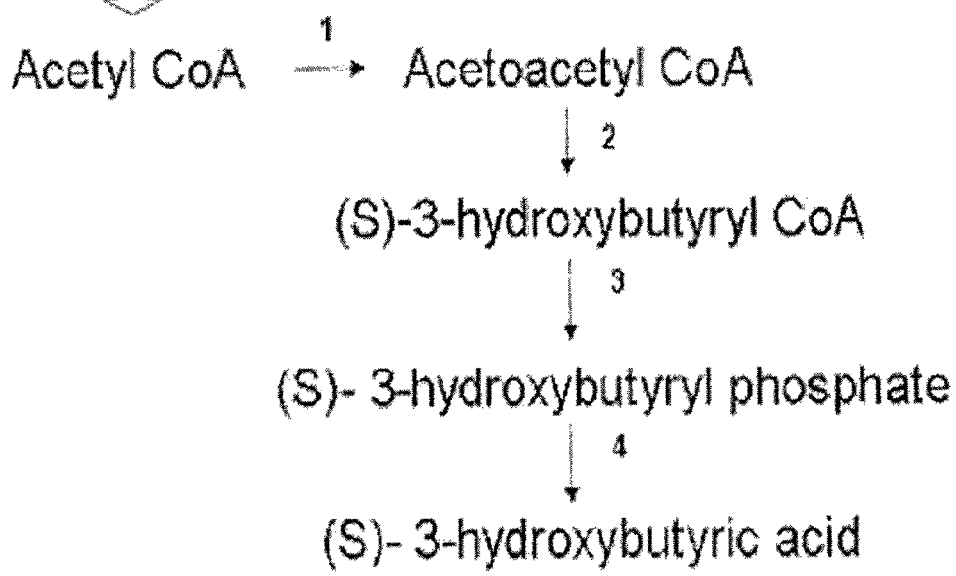
FIG. 3 shows a synthetic pathway of (S)-3-HB esters.

The present invention also provides a recombinant microorganism for preparing (S)-3-hydroxybutyrate ester, which is transformed with a gene encoding β-ketothiolase, a gene encoding (S)-3-hydroxybutyryl CoA dehydrogenase, a gene encoding acyl CoA hydrolase and a gene encoding lipase.
As shown in FIG. 3, the recombinant microorganism transformed with a gene encoding β-ketothiolase, a gene encoding (S)-3-hydroxybutyryl CoA dehydrogenase, a gene encoding acyl CoA hydrolase and a gene encoding lipase according to the present invention produces (S)-3-hydroxybutyrate ester by esterification of (S)-3-hydroxybutyric acid, which is produced through the biosynthetic pathway of (S)-3-hydroxybutyric acid shown in FIG. 1, by lipase.

In the present invention, any one of the genes encoding the above-mentioned enzymes including β-ketothiolase, (S)-3-hydroxybutyryl CoA dehydrogenase, acyl CoA hydrolase and lipase can be used without limitation. While specific genes are used in the following examples, it will be clearly understood by those skilled in the art that the scope of the present invention is not limited to the specific genes disclosed herein. In one embodiment of the present invention, a gene encoding β-ketothiolase may be represented by SEQ ID NO: 1.

In one embodiment of the present invention, a gene encoding (S)-3-hydroxybutyryl CoA dehydrogenase may be represented by SEQ ID NO: 2 or 3. In one embodiment of the present invention, acyl CoA hydrolase may be (S)-3-hydroxybutyryl CoA hydrolase. In one embodiment of the present invention, the (S)-3-hydroxybutyryl CoA hydrolase may be coded by a base sequence of SEQ ID NO: 4. In the present invention, a vector refers to a DNA construct containing a DNA sequence which is operably linked to an expression control sequence suitable for expressing DNA in a suitable host. The vector may be a plasmid, a phage particle, or just a latent genomic insert. When a suitable host is transformed with the vector, the vector may be self-replicable or function regardless of host genome, or may be integrated with the host genome in some cases. A plasmid is the most common type of vector, and thus the terms plasmid and vector are used interchangeably below. However, the present invention also includes different forms of vectors, which are known or considered to perform the same function as conventional vectors in the art.

The expression control sequence refers to a DNA sequence that is essential to expression of a coding sequence operably linked to other DNA sequences in a specific host cell. This control sequence includes a promoter for initiating transcription, a random operator sequence for controlling the transcription, a sequence coding for a suitable mRNA ribosome binding site, and a sequence for controlling termination of transcription and translation. For example, a control sequence specific to a prokaryote includes a promoter, a random operator sequence and a ribosome binding site. For a eukaryote, a control sequence includes a promoter, a polyadenylation signal, and an enhancer. In a plasmid, a promoter is the factor with the greatest effect on amount of gene expression. For high expression, a SRα promoter or a cytomegalovirus-derived promoter may be used.

To express the DNA sequence of the present invention, any one of various expression control sequences may be applied to a vector. For example, useful expression control sequences include early and late promoters of SV40 or adenovirus, a lac system, a trp system, a TAC or TRC system, T3 and T7 promoters, a major operator and promoter region of l phage, a control region of fd code protein, a promoter for 3-phosphoglycerate kinase or other glycolytic enzymes, promotors for the phosphatases, e.g., Pho5, a promoter for a yeast alpha-mating system, other sequence of construct known for controlling the expression of genes of prokaryote, eukaryote or virus thereof, and combinations thereof.

A nucleic acid is operably linked when is arranged in a functional relationship with another nucleic acid sequence. The nucleic acid may be a gene and a control sequence(s) linked to be capable of expressing the gene when it binds to a control sequence(s) (e.g., transcription-activating protein). For example, DNA for a pre-sequence or a secretory leader is operably linked to DNA encoding polypeptide when expressed as pre-protein participating in secretion of polypeptide; a promoter or an enhancer is operably linked to a coding sequence when affecting the transcription of the sequence; and a ribosome binding site is operably linked to a coding sequence when affecting the transcription of the sequence, or to a coding sequence when arranged to facilitate translation. Generally, the term operably linked means that the DNA linked sequences are contiguous, and in the case of the secretory leader, are contiguous and present in a reading frame. However, an enhancer is not necessarily contiguous. The linkage between these sequences is performed by ligation at a convenient restriction enzyme site. However, when the site does not exist, a synthetic oligonucleotide adaptor or a linker is used according to a conventional method.

The term expression vector used herein generally means a double-stranded DNA fragment functioning as a recombinant carrier into which a heterologous DNA fragment is inserted. Here, the heterologous DNA means a hetero-type DNA, which is not naturally found in a host cell. The expression vector may be self-replicable regardless of host chromosomal DNA once in a host cell, and may produce several copies of the vector and (heterologous) DNA inserted thereinto.

As is well known in the art, in order to increase an expression level of a transfected gene in a host cell, a corresponding gene should be operably linked to transcription and translation expression control sequences which are operated in a selected expression host. Preferably, the expression control sequences and the corresponding gene are included in one expression vector together with a bacterial selection marker and a replication origin. When an expression host is a eukaryotic cell, an expression vector should further include an expression marker which is useful in a eukaryotic expression host.

In the present invention, various vectors may be used as a recombinant vector, including a plasmid vector, a bacteriophage vector, a cosmid vector, and a yeast artificial chromosome (YAC) vector. For example, the plasmid vector may have a constitution including (a) a replication origin for effective replication to have several hundreds of copies in one host cell, (b) an antibiotic-resistance gene for selecting a host cell transformed with the plasmid vector, and (c) a restriction enzyme site into which a foreign DNA fragment is capable of being inserted. Although there is no suitable restriction enzyme site, the vector may be easily ligated with a foreign DNA using a synthetic oligonucleotide adaptor or a linker according to a conventional method.

The recombinant vector according to the present invention may be introduced into a suitable host cell by a conventional method. As host cells, bacterial, yeast or fungal cells may be used, however the present invention is not limited thereto. The host cells in the present invention preferably include prokaryotic cells, e.g., *E. coli*. Preferable strains of *E. coli* include *E. coli* strain BL21, *E. coli* strain DH5a, *E. coli* strain JM101, *E. coli* K12 strain 294, *E. coli* strain W3110, *E. coli* strain X1776, *E. coli* XL-1Blue (Stratagene) and *E. coli* B. Further, other *E. coli* strains such as FMB101, NM522, NM538 and NM539, and other prokaryotic species and genera may be used. In addition to the *E. coli strains, Agrobacterium* genera strains such as *Agrobacterium* A4, *Bacilli* genera strains such as *Bacillus subtilits*, other enterobacteria such as *Salmonella typhimurium* and *Serratia marcescens*, and various *Pseudomonas* genera strains may be used as host cells, but the present invention will not be limited thereto.

Further, the transformation of the prokaryotic cell may be easily accomplished by a potassium chloride method described in section 1.82 of Sambrook et al. (supra). Alternatively, electroporation may also be used to transform these cells (Neumann et al., EMBO J., 1:841 (1982)).

The present invention also provides a method of preparing (S)-3-hydroxybutyric acid comprising constructing a recombinant microorganism, which is transformed with a gene encoding β-ketothiolase, a gene encoding (S)-3-hydroxybutyryl CoA dehydrogenase and a gene encoding acyl CoA hydrolase, and culturing the recombinant microorganism. The microorganisms may be cultured in a medium containing a suitable carbon source.

The present invention also provides a method of preparing (S)-3-hydroxybutyric acid which is characterized by reacting a culture or a cell extract of the recombinant microorganism with a substrate selected from the group consisting of acetyl-CoA, acetoacetyl CoA and (S)-3-hydroxybutyryl CoA.

The present invention also provides a method of preparing (S)-3-hydroxybutyrate ester comprising constructing a recombinant microorganism for preparing (S)-3-hydrozybutyrate ester, which is transformed with a gene encoding O-ketothiolase, a gene encoding (S)-3-hydroxybutyryl CoA dehydrogenase, a gene encoding acyl CoA hydrolase and a gene encoding lipase, and culturing the recombinant microorganism.

Hereinafter, the present invention will be described in more detail through examples. However, these examples are merely provided to explain the present invention, not to limit its scope.

EXAMPLES

Example 1

Construction of Recombinant Vector Containing Genes Encoding β-ketothiolase and (S)-3-hydroxybutyryl CoA dehydrogenase (pTacReA-HBD)

First, Ralstonia eutropha H16 strain (ATCC 17699) was cultured in a 3 ml LB liquid medium for 18 hours and the culture medium was centrifuged to harvest cells. The cells were washed with 10 ml Tris buffer. Then, a chromosome of the strain was isolated using a Wizard Genomic DNA Purification Kit (Promega, USA).

The isolated chromosome was used as a template to amplify β-ketothiolase gene (SEQ ID NO: 1) derived from the Ralstonia eutropha strain using ReAf-EcoRI primer (SEQ ID NO: 5) and ReAb1259 primer (SEQ ID NO: 6). 250 uM dNTP, 20 pmol of each primer, 1.5 mM $MgCl_2$, 10 ul 10× buffer, 100 ng DNA template and 5 units of pfu polymerase were added to a 100 ul PCR mixture, and underwent 25 cycles of initial denaturation at 95° C. for 5 minutes, denaturation at 95° C. for 1 minute, annealing at 50° C. for 1 minute and polymerization at 72° C. for 1 minute.

```
ReAf-EcoRI:
                                        (SEQ ID NO: 5)
5-ggaattc ATGACTGACGTTGTCATCGTATCC-3

ReAb1259:
                                        (SEQ ID NO: 6)
5-GTC CAC TCC TTG ATT GGC TTC G-3
```

Under the same conditions, (S)-3-hydroxybutyryl CoA dehydrogenase gene (SEQ ID NO:2) derived from *Clostridium acetobutylicum* strain (ATCC 824) was amplified using Cahbdf primer (SEQ ID NO: 7) and Cahbdb-XbaI primer (SEQ ID NO: 8).

```
Cahbdf:
                                        (SEQ ID NO: 7)
5-GAA GCC AAT CAA GGA GTG GAC ATGAAAAAGGTATGTGTTA

TAGG-3

Cahbdb-XbaI:
                                        (SEQ ID NO: 8)
5-GC TCTAGA TTA TTT TGA ATA ATC GTA GAA ACC-3
```

Figure 4:
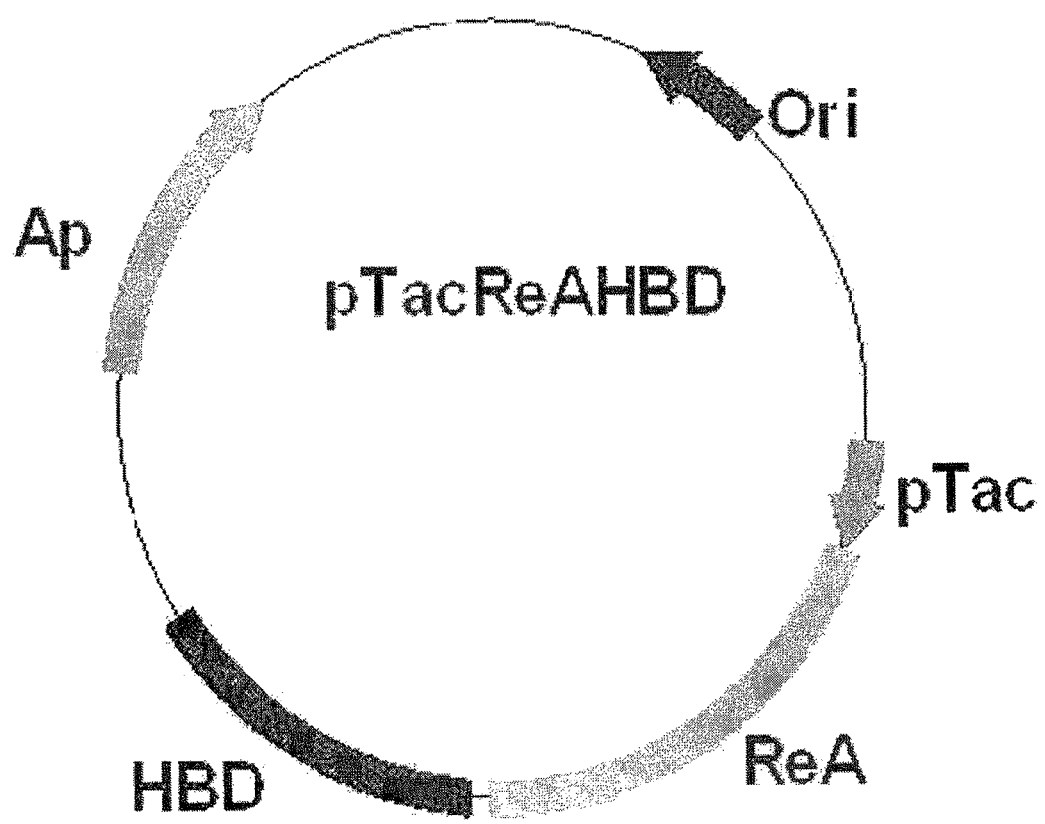
FIG. 4 shows a cleavage map of pTacReA-HBD series vector.

The amplified genes were purified on a 1% agarose gel, and then both were fused together by PCR. First, two genes each having a concentration of 1 pmol were mixed together to be used as a template for PCR and amplified under the same conditions as described above, except that polymerization was performed for 2.5 minutes. The amplified genes were purified on a 1% agarose gel and then cleaved with EcoRI and XbaI restriction enzymes to obtain DNA fragments. The fragments were inserted into pTac99A vector (Park and Lee, J. Bacteriol. 185, 5391-5397, 2003), which also was cleaved with the same restriction enzymes, by ligation to construct pTacReA-HBD (see FIG. 4).

Example 2

Construction of Recombinant Vectors Containing Gene Encoding (S)-3-hydroxybutyryl CoA hydrolase (pET21aBCH, pET28bBCH and pK28BCH)

First, *Bacillus cereus* (ATCC 14579) strain was cultured in an LB liquid medium for 18 hours, and then its chromosome was isolated by the same method as described in Example 1. The isolated chromosome was used as a template to amplify 3-hydroxyisobutyryl CoA hydrolase (BCH) gene (SEQ ID NO: 4) using ACH_NdeI primer (SEQ ID NO: 9) and ACH_BamHI primer (SEQ ID NO: 10) by PCR under the same conditions as described in Example 1.

```
ACH_NdeI:
                                        (SEQ ID NO: 9)
5-CGC CAT ATG ACT GAA CAA GTT TTA TTT-3

ACH_BamHI:
                                        (SEQ ID NO: 10)
5-ATA GGA TCC TTA TGC ATT AAG TAA GTT AAA G-3
```

Figure 5:
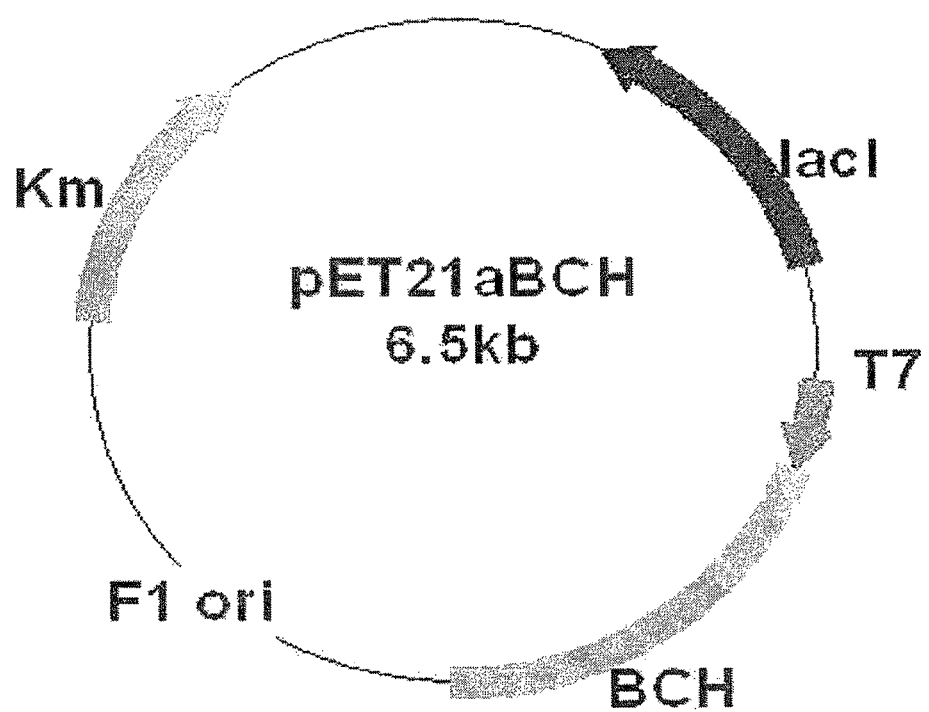
FIG. 5 shows a cleavage map of pET21aBCH series vector.

The amplified genes were purified under the same conditions as described in Example 1 and cleaved with restriction enzymes NdeI and BamHI. The gene fragments were respectively inserted into pET21a (Novagen, USA), pET28B (Novagen, USA) and pK28, which were also cleaved with the same restriction enzymes, by ligation to construct pET21aBCH, pET28bBCH and pK28BCH (see FIG. 5).

The pK21 vector was constructed in vitro by cleaving pET21a vector with restriction enzymes BglII and XbaI, amplifying a promoter-suspicious site of EZ::TN<KAN2> transposon (Epicenter, USA; Cat#: MOD 1503) using KAN2-P-bglII primer (SEQ ID NO: 11) and KAN2-P-XbaI primer (SEQ ID NO: 12) by PCR, cleaving the PCR product with the same restriction enzymes and ligating them together. The amplified DNA sequence is shown as SEQ ID NO: 13.

```
KAN2-P-bglII:
                                        (SEQ ID NO: 11)
TATA AGA TCT CAA CCA TCA TCG ATG AAT TGT KAN2-P-XbaI:
                                        (SEQ ID NO: 12)
TAT TCT AGA AAC ACC CCT TGT ATT ACT GTT EZ::TN<KAN2> transposon:
                                        (SEQ ID NO: 13)
5-TACACATCTCAACCATCATCGATGAATTGTGTCTCAAAATCTCTGAT

GTTACATTGCACAAGATAAAAATATATCATCATGAACAATAAAACTGTCT

GCTTACATAAACA GTAATACAAG GGGTGTT-3
```

Example 3

Construction of Recombinant Vectors Containing Gene Encoding (S)-3-hydroxybutyryl CoA dehydrogenase (pET21aHBD and pK21HBD)

First, *Clostridium acetobutylicum* (ATCC 824) isolated in Example 1 was used as a template to amplify (S)-3-hydroxybutyryl CoA dehydrogenase gene (SEQ ID NO: 2) using hbd_NdeI primer (SEQ ID NO: 14) and hbd_BamHI primer (SEQ ID NO: 15) under the same conditions as described in Example 1.

```
hbd_NdeI:
                                    (SEQ ID NO: 14)
5-ATA CAT ATG AAA AAG GTA TGT GTT ATA GGT GCA GGT-3 hbd_BamHI:
                                    (SEQ ID NO: 15)
5-ATA GGA TTC TTA TTT TGA ATA ATC GTA GAA ACC TTT-3
```

Figure 6:
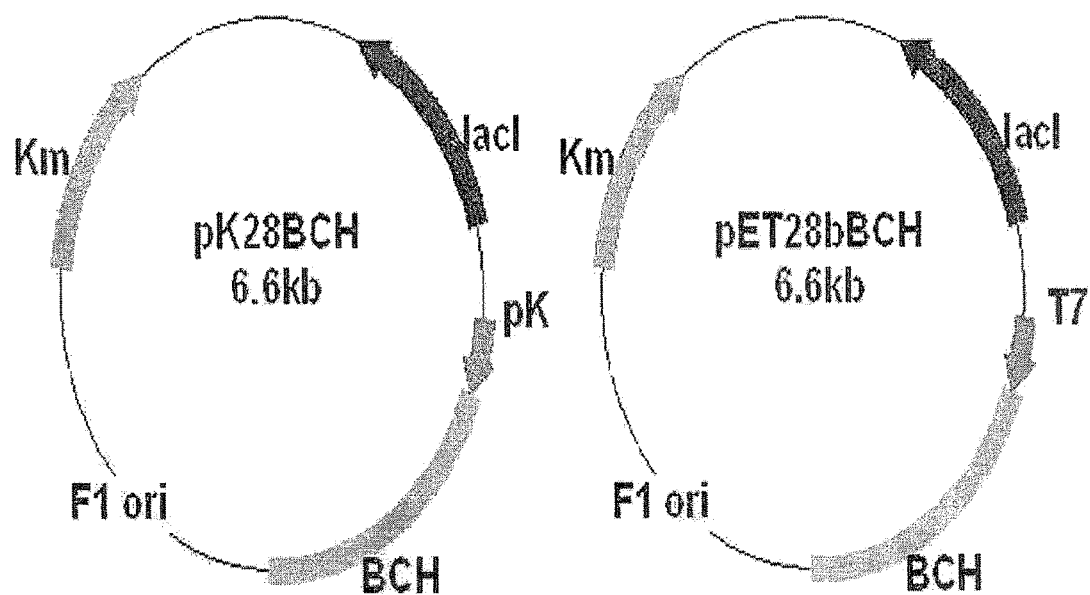
FIG. 6 shows cleavage maps of pK28BCH, pET28bBCH series vectors.
Figure 7:
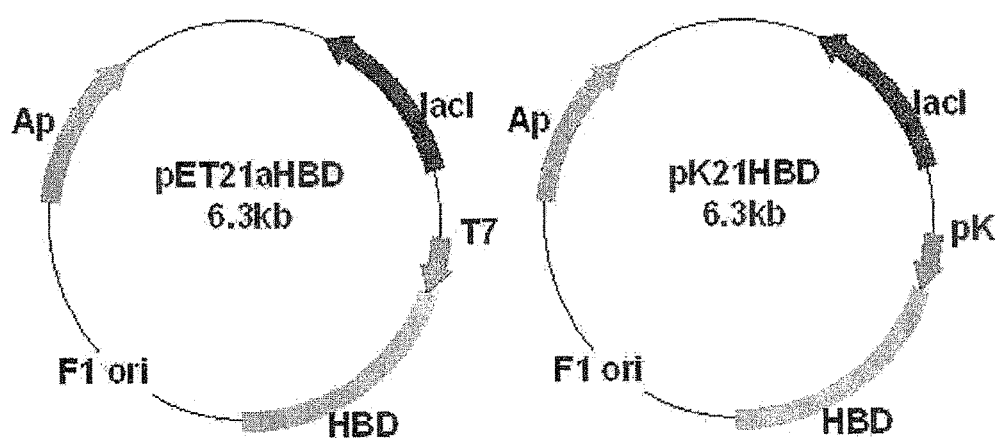
FIG. 7 shows cleavage maps for pET21aHBD and pK21HBD series vectors.

The amplified genes were cleaved with NdeI and BamHI restriction enzymes and ligated with pET21a vector and pK21 vector, which were cleaved with the same restriction enzymes to construct pET21aHBD and pK21HBD (see FIG. 6).

Example 4

Detection of (S)-3-hydroxybutyryl CoA dehydrogenase (HBD) Gene Activity pET21aHBD constructed in Example 3 was introduced into *E. coli* BL21(DE3) to transform by electroporation, and then the transformed *E. coli* BL21(DE3) cell was plated on an LB ampicillin plate and grown overnight at 37° C. The cultured colony was inoculated into a 3 ml LB liquid medium containing 100 ug/ml ampicillin, and then grown at 200 rpm and 37° C. in a shaking incubator (Jeiotech, Korea) to have an $OD_{600}$ level of 0.5. Then, IPTG was added to the culture at a final concentration of 1 mM to induce protein expression and the culture was grown overnight. After that, the culture was centrifuged to harvest cells, the cells were disrupted by ultrasonication and then centrifuged to obtain a cell-free extract. The obtained cell-free extract was used as a sample to detect enzyme activity.

The activity of (S)-3-hydroxybutyryl CoA dehydrogenase in the sample was detected by HPLC (Shimadzu, Japan) from (S)-3-hydroxybutyryl CoA produced after a mixture of 1 mM acetoacetyl CoA, 3 mM NADH and 20 ul of 5 mg/ml cell-free extract was reacted at 37° C. for 5 minutes.

For HPLC, a 97:3 mixture of water and acetonitrile as a mobile phase was streamed for 5 minutes, and a ratio of acetonitrile was increased up to 15% for 25 minutes. Here, solvent flow was 1 ml/min, C18 Capcel PAK (Shisheido, Japan) was used as a column, and (S)-3-hydroxybutyryl CoA was detected at 210 nm.

As a result, it could be confirmed that the *E. coli* BL21(DE3) transformed with the recombinant vector containing a (S)-3-hydroxybutyryl CoA dehydrogenase gene constructed in Example 3 produces active (S)-3-hydroxybutyryl CoA dehydrogenase, as shown in Table 1.

TABLE 1

| Enzyme activity of (S)-3-hydroxybutyryl CoA dehydrogenase | | |
|---|---|---|
|  | HBD | Control |
| Conversion Ratio | 75% | 0% |

Example 5

Detection of Activity of (S)-3-hydroxybutyryl CoA hydrogenase (BCH) Gene *E. coli* BL21 transformed with pET21aBCH constructed in Example 2, by the same method as described in Example 4, was incubated to obtain a cell-free extract, which was used to detect the activity of 3-hydroxyisobutyryl CoA hydrolase.

The activity of 3-hydroxyisobutyryl CoA hydrolase was detected by HPLC (Shimadzu, Japan) from 3-hydroxyburyric acid, after a mixture of 1 mM (S)-3-hydroxybutyryl CoA and 20 ul of 5 mg/ml cell-free extract was reacted at 37° C. for 30 minutes. HPLC was performed under the same conditions as described in Example 4.

As a result, it can be confirmed that *E. coli* BL21(DE3) transformed with the recombinant vector containing (S)-3-hydroxybutyryl CoA hydrolase gene constructed in Example 2 produced active 3-hydroxyisobutyryl CoA hydrolase, as shown in Table 2.

TABLE 2

| Activity of 3-hydroxyisobutyryl CoA hydrolase (BCH) | | |
|---|---|---|
|  | BCH | Control |
| Conversion ratio | 73.5% | 28% |

Example 6

Preparation of (S)-3-hydroxybutyric Acid Using Cell Extract of Microorganism Transformed with Vector Containing β-ketothiolase, HBD and BCH Genes *E. coli* BL21(DE3) was simultaneously transformed with the pTacReA-HBD, pET21aBCH and pK28BCH constructed in Examples 1 to 3 by electroporation, and then cell-free extracts were harvested by the same method as described in Example 4 to be used in detection of enzyme activities.

Production of (S)-3-hydroxybutyric acid was detected by HPLC (Shimadzu, Japan) from a mixture of 1 mM acetyl CoA, 3 mM NADH and 20 ul of 5 mg/ml cell-free extract after reacting at 37° C. for 30 minutes.

Analysis was performed by the same method as described in Example 5 using CoA produced by hydrolysis.

As a result, it can be confirmed that *E. coli* BL21(DE3) transformed with pTacReA-HBD, pET21aBCH and pK28BCH produced active β-ketothiolase, 3-hydroxyisobutyryl CoA hydrolase and (S)-3-hydroxybutyryl CoA dehydrogenase, as shown in Table 3.

TABLE 3

| Production of (S)-3-hydroxybutyric acid using cell extract of recombinant *E. coli*. | | |
|---|---|---|
|  | Recombinant *E. coli* | Control |
| Conversion Ratio | 7.84% | 0.01% |

Example 7

In-vivo Construction of Vector Containing β-ketothiolase, HBD, BCH Genes, Microorganism Transformed with Recombinant Vector, and (S)-3-hydroxybutyric Acid Using The Same *E. coli* BL21(DE3) was transformed with both pTacReA-HBD and pET28bBCH constructed in Examples 1 and 2 by electroporation, and then plated on an LB plate containing 100 ug/ml ampicillin and 50 ug/ml kanamycin. The cells were grown overnight at 37° C. Two colonies were inoculated into a 15 ml tube (Falcon, USA) comprising LB liquid medium containing 100 ug/ml ampicillin, and grown overnight in a shaking incubator at 200 rpm and 37° C. The incubated cells were inoculated again into an LB liquid medium containing 50 ml of 2% glucose and 100 ug/ml ampicillin, and grown in a shaking incubator at 200 rpm and 37° C. When $OD_{600}$ reached 0.5, IPTG was added to the culture at a final concentration of 1 mM to induce protein expression, and then the culture of cells was grown overnight.

Afterward, the culture was centrifuged to harvest a supernatant, and a quantitative analysis of 3-hydroxybutyric acid was performed by HPLC. For HPLC, water containing 0.01N sulfuric acid was used as a mobile phase, and water flow was 0.6 ml/min. A column used herein was Aminex87H (Bio-rad, USA), and production of 3-hydroxybutyric acid was detected by a refractive index (RI) detector. The results are shown in Table 4.

TABLE 4

Quantitative data of (S)-3-hydroxybutyric acid

|  | DCW | (S)-3-HB(g/L) After induction | | | Acetate (g/L) final | Glucose consumed (g/L) |
| --- | --- | --- | --- | --- | --- | --- |
|  |  | 0 h | 5 h | 24 h |  |  |
| Sample 1 | 0.74 g/L | 0 | 0.190 | 0.348 | 2.12 | 8.36 |
| Sample 2 | 1.6 g/L | 0 | 0.193 | 0.370 | 2.01 | 9.10 |

Figure 8:
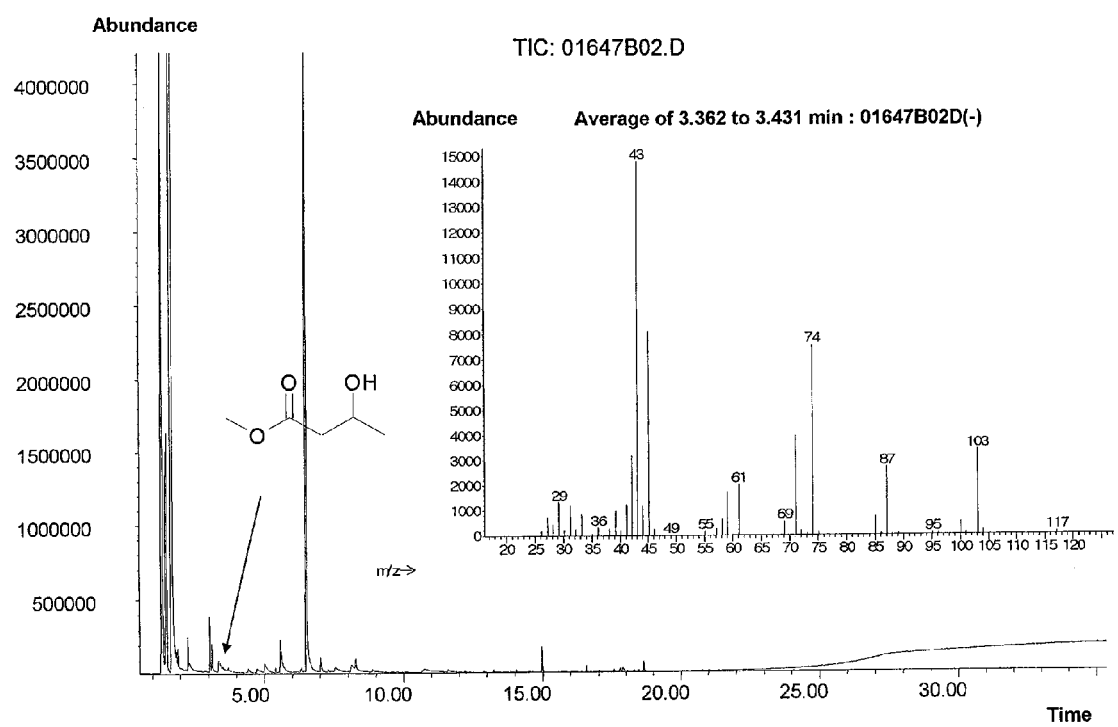
FIG. 8 shows GC-MSD analysis results obtained by methylation of (S)-3-HB produced according to the present invention.
Figure 9:
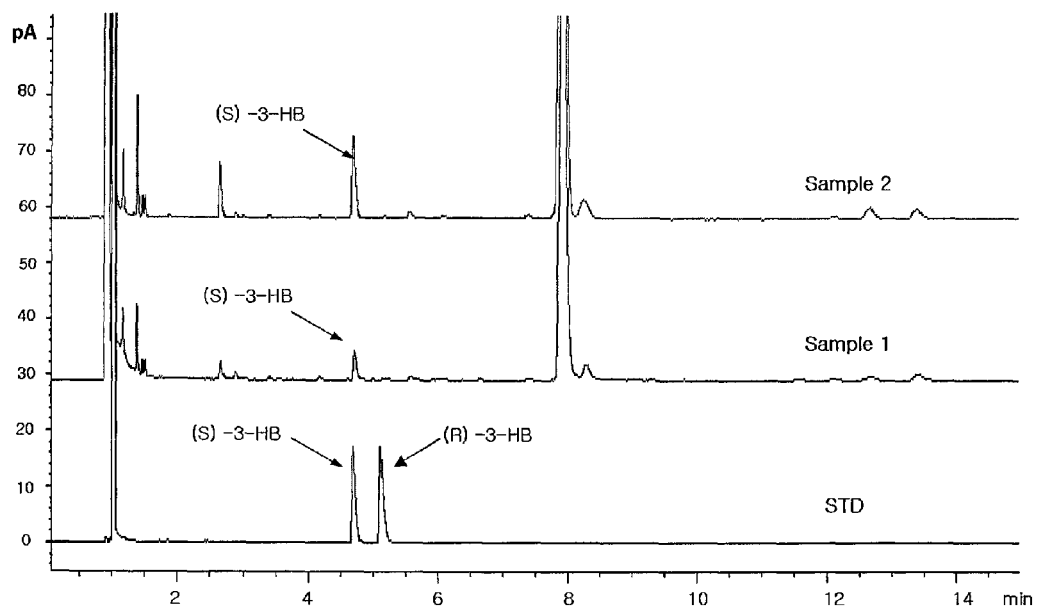
FIG. 9 shows chirality analysis result by methylation of (S)-3-HB produced according to the present invention.

For more accurate qualitative and quantitative analyses, the culture containing 3-hydroxybutyric acid was freeze-dried, and then the product was methylated to perform GC-MSD (mass spectroscopy) and a chirality analysis for methyl (S)-3-hydroxyburyrate. The analyses were performed by gas chromatography (Agilent, USA), and the analysis conditions are shown in Table 5. By mass spectroscopy, the product could be identified as 3-hydroxybutyric acid, and the results are shown in FIGS. 8 and 9. According to the chirality analysis, (S)-3-hydroxybutyric acid having an optical density of at least 99.9% ee was produced, and an Enantiomeric excess (ee) level was determined by the following Formula (1):

$$ee^S = (C_S - C_R)/(C_S + C_R) \times 100 \quad (1)$$

TABLE 5

Conditions for GC MSD and GC Chirality Analyses

| GC-MSD Qualitative Analysis | Oven temperature: 50° C./5 min-10° C./min-320° C./10 min<br>Injector temperature: 320° C.<br>Detector temperature: 320° C.<br>Injector Split ratio: 20/1 |
| --- | --- |
| GC-FID Quantitative Analysis (Chirality) | Injector 160° C., 3 ml/min He, 20:1 s/s ratio<br>Oven 80° C./15 min<br>Detector make-up flow: 30 mL/min<br>Air flow: 300 mL/min<br>H2 flow: 30 mL/min<br>Temperature: 160° C.<br>Column: G-TA (30 m × 0.25 mm) |

Example 8

Construction of pET21aBCH-ReA-HBD and pET21aBCH-ReA-ReHBD Vectors

By the same method as described in Example 1, an R. eutropha-derived HBD (ReHBD) gene (SEQ ID NO: 3) was amplified using ReHBD-RBS-UP primer and ReHBD-DN-XhoI primer.

ReHBD-RBD-UP:
(SEQ ID NO: 16)
5-GAAGCCAATCAAGGAGTGGACATGAGCATCAGGACAGTGGG-3

ReHBD-DN-XhoI:
(SEQ ID NO: 17)
5-ATACTCGAGTTACTTGCTATAGACGTACACGCCGCGGCC-3

Under the same conditions as described in Example 1, the ReA gene was fused with the ReHBD gene using ReAf-EcoRI primer (SEQ ID NO: 5) and ReHBD-DN-XhoI primer (SEQ ID NO: 17) to produce a ReAReHBD gene. Further, the pTacReA-HBD vector constructed in Example 1 was used as a template to amplify the ReA-HBD gene using ReAf-EcoRI primer and ReHBD-DN-XhoI primer. The fused and amplified genes were cleaved with EcoRI and XhoI restriction enzymes, pET21aBCH constructed in Example 2 was also cleaved with the same restriction enzymes, and then they were purified. The gene fragments were inserted into the vectors by ligation, and thus pET21aBCH-ReA-HBD and pET21aBCH-ReA-ReHBD were finally constructed.

HBD-DN-XhoI:
(SEQ ID NO: 18)
5-ATACTCGAGTTATTTTGAATAATCGTAGAAACCTTTTCCTG-3

Example 9

Figure 10:
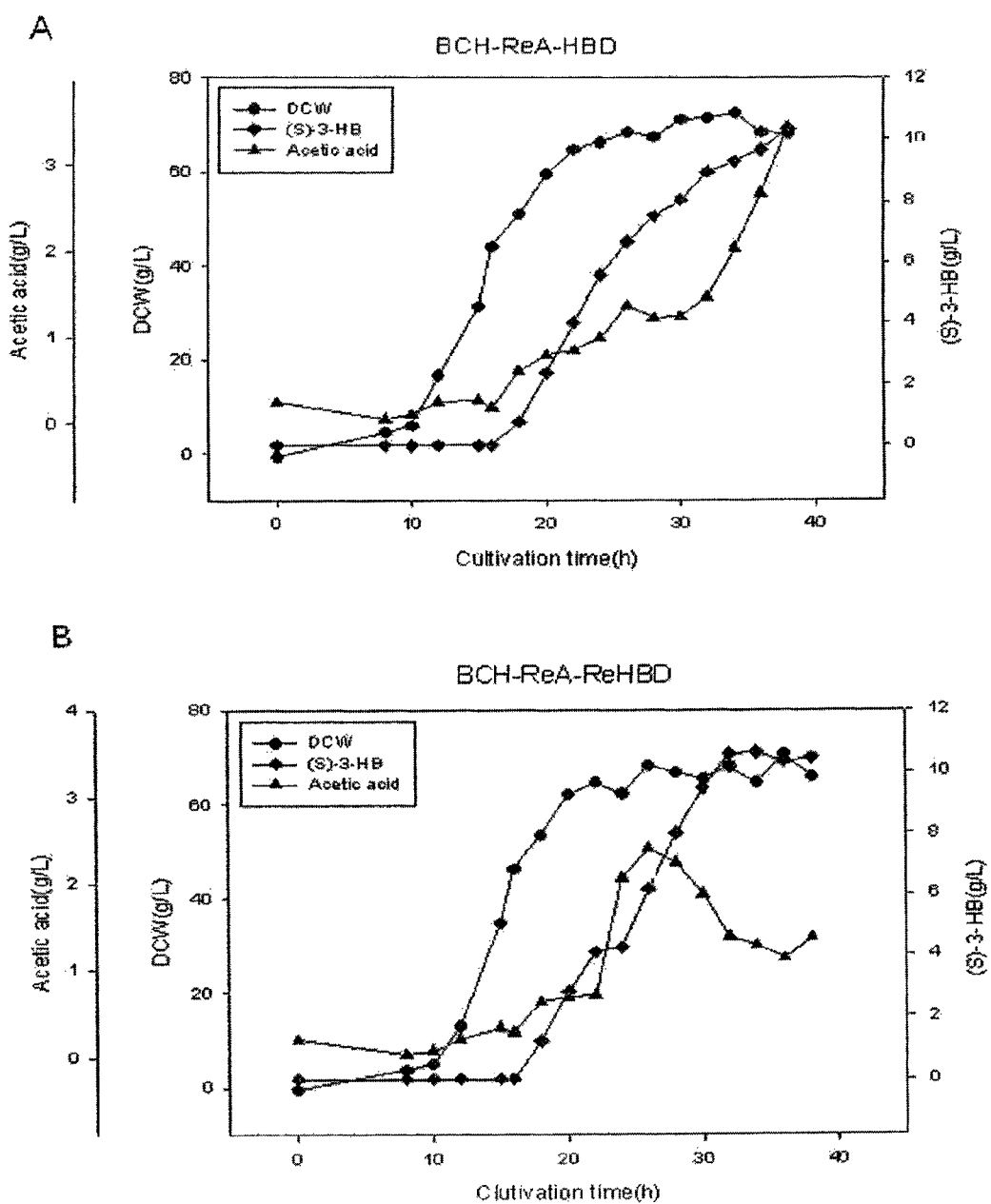
FIG. 10 shows time profiles when (S)-3-HB is produced through fed-batch culture according to the present invention.

Construction of (S)-3-hydroxybutyric Acid Using E. coli Transformed with pET21aBCH-ReA-HBD and pET21aBCH-ReA-ReHBD Vectors E. coli Codon Plus (DE3) was transformed with pET21aBCH-ReA-HBD or pET21a-BCH-ReA-ReHBD constructed in Example 8 by electroporation, and then plated on an LB/ampicillin plate and grown overnight at 37° C. Two colonies were inoculated into a 15 ml disposable tube (Falcon, USA) containing a 3 ml LB/ampicillin medium and grown overnight in a shaking incubator at 200 rpm and 37° C. The incubated cells were inoculated again into an MR liquid medium containing 100 ml of 2% glucose and grown in a shaking incubator at 200 rpm and 37° C. for 10 hours. Then, the culture of cells was inoculated into a 1.5 L fermenter to incubate. After incubation, when $OD_{600}$ reached 120, IPTG was added at a final concentration of 1 mM to induce protein expression, and (S)-3-hydroxybutyric acid produced was analyzed every 2 hours by the same method as described in Example 7. As a result, about 10 g/L of (S)-3-HB was produced (see FIG. 10 and Table 6).

TABLE 6

Preparation of (S)-3-hydroxybutyric acid using E. coli transformed with pET21aBCH-ReA-HBD and pET21aBCH-ReA-ReHBD vectors

| Reaction Time (h) | | HBD (g/L) | | | | ReHBD (g/L) | | | |
| --- | --- | --- | --- | --- | --- | --- | --- | --- | --- |
| Incubation | Induction of Expression | DCW | Glu | S3HB | AA | DCW | Glu | S3HB | AA |
| 0.0 | | −0.7 | 20.1 | | 0.2 | −0.3 | 21.1 | | 0.2 |
| 8.0 | | 4.5 | 17.0 | | 0.0 | 3.6 | 18.9 | | 0.0 |
| 10.0 | | 6.0 | 10.5 | | 0.1 | 5.1 | 14.1 | | 0.1 |
| 12.0 | | 16.7 | 5.6 | | 0.2 | 12.8 | 11.9 | | 0.2 |

TABLE 6-continued

Preparation of (S)-3-hydroxybutyric acid using *E. coli* transformed with pET21aBCH-ReA-HBD and pET21aBCH-ReA-ReHBD vectors

| Reaction Time (h) | | HBD (g/L) | | | | ReHBD (g/L) | | | |
|---|---|---|---|---|---|---|---|---|---|
| Incubation | Induction of Expression | DCW | Glu | S3HB | AA | DCW | Glu | S3HB | AA |
| 15.0 |  | 31.2 | 9.1 |  | 0.3 | 34.7 | 7.9 |  | 0.3 |
| 16.0 | 0.0 | 44.2 | 5.0 |  | 0.2 | 46.2 | 5.7 |  | 0.3 |
| 18.0 | 2.0 | 51.1 | 6.2 | 0.8 | 0.6 | 53.5 | 7.3 | 1.2 | 0.6 |
| 20.0 | 4.0 | 59.7 | 2.5 | 2.4 | 0.8 | 62.2 | 5.6 | 2.8 | 0.7 |
| 22.0 | 6.0 | 64.8 | 5.3 | 4.0 | 0.8 | 64.7 | 2.0 | 4.1 | 0.7 |
| 24.0 | 8.0 | 66.3 | 5.0 | 5.6 | 1.0 | 62.3 | 7.3 | 4.2 | 2.0 |
| 26.0 | 10.0 | 68.5 | 3.6 | 6.7 | 1.4 | 68.3 | 7.8 | 6.2 | 2.4 |
| 28.0 | 12.0 | 67.5 | 7.0 | 7.5 | 1.2 | 66.9 | 4.0 | 8.0 | 2.2 |
| 30.0 | 14.0 | 71.3 | 5.6 | 8.1 | 1.2 | 65.4 | 3.3 | 9.5 | 1.9 |
| 32.0 | 16.0 | 71.6 | 3.6 | 8.9 | 1.5 | 68.1 | 2.8 | 10.6 | 1.4 |
| 34.0 | 18.0 | 72.5 | 3.6 | 9.3 | 2.0 | 64.7 | 4.3 | 10.6 | 1.3 |
| 36.0 | 20.0 | 68.4 | 2.7 | 9.7 | 2.7 | 70.6 | 4.8 | 10.3 | 1.1 |
| 38.0 | 22.0 | 68.2 | 2.3 | 10.3 | 3.4 | 65.8 | 4.6 | 10.4 | 1.4 |

While specific parts of the present invention have been described in detail, it will be clearly understood by those skilled in the art that the above descriptions and Examples are not intended to limit the scope of the present invention, which is defined by the accompanying claims and their equivalents.

It will be understood by those skilled in the art that various changes in form and details may be made therein without departing from the spirit and scope of the invention as defined by the appended claims.

The invention claimed is:

1. A recombinant microorganism for preparing (S)-3-hydroxybutyric acid, which is transformed with a gene encoding β-ketothiolase, a gene encoding (S)-3-hydroxybutyryl CoA dehydrogenase and a gene encoding acyl CoA hydrolase.

2. The recombinant microorganism according to claim 1, wherein the gene encoding β-ketothiolase is SEQ ID NO: 1.

3. The recombinant microorganism according to claim 1, wherein the gene encoding (S)-3-hydroxybutyryl CoA dehydrogenase is SEQ ID NO: 2 or SEQ ID NO: 3.

4. The recombinant microorganism according to claim 1, wherein the acyl CoA hydrolase is (S)-3-hydroxybutyryl CoA hydrolase.

5. The recombinant microorganism according to claim 4, wherein the (S)-3-hydroxybutyryl CoA hydrolase is encoded by SEQ ID NO: 4.

6. The recombinant microorganism according to claim 1, wherein the recombinant microorganism is transformed with a gene encoding β-ketothiolase, a gene encoding (S)-3-hydroxybutyryl CoA dehydrogenase and a gene encoding acyl CoA hydrolase using at least one recombinant vector.

7. A method of preparing (S)-3-hydroxybutyric acid, comprising:
   constructing a recombinant microorganism transformed with a gene encoding β-ketothiolase, a gene encoding (S)-3-hydroxybutyryl CoA dehydrogenase and a gene encoding acyl CoA hydrolase; and
   culturing the recombinant microorganism.

8. A method of preparing (S)-3-hydroxybutyric acid, comprising:
   reacting a culture or cell extract of recombinant microorganisms transformed with a gene encoding β-ketothiolase, a gene encoding (S)-3-hydroxybutyryl CoA dehydrogenase and a gene encoding acyl CoA hydrolase with a substrate selected from the group consisting of acetyl CoA, acetoacetyl CoA and (S)-3-hydroxybutyryl CoA.

\* \* \* \* \*